(12) United States Patent
Sen et al.

(10) Patent No.: US 7,119,226 B2
(45) Date of Patent: Oct. 10, 2006

(54) PROCESS FOR THE CONVERSION OF METHANE

(75) Inventors: Ayusman Sen, State College, PA (US); Minren Lin, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 11/105,245

(22) Filed: Apr. 13, 2005

(65) Prior Publication Data

US 2006/0100458 A1     May 11, 2006

Related U.S. Application Data

(60) Provisional application No. 60/563,717, filed on Apr. 20, 2004.

(51) Int. Cl.
*C07C 309/00*     (2006.01)
(52) U.S. Cl. ..................................................... 562/123
(58) Field of Classification Search ................... None
See application file for complete search history.

(56) References Cited

U.S. PATENT DOCUMENTS

| 2,492,983 A | 1/1950 | Grosse et al. |
| 3,927,189 A | 12/1975 | Jayawant |

OTHER PUBLICATIONS

M.G.Axelrod, et al., Natural Gas: Fuel or Feedstock, Natural Gas Conversion II, 1994, 93-101, Elvevier.
Natural Gas Conversion VI, Table of Contents, ix-xiii, 2001, Elsevier.
A. Sen, Catalytic Functionalization of Carbon-Hydrogen and Carbon-Carbon Bonds in Protic Media, Acc. Chem. Res. 1998, 550-557.
S. Stahl, et al., Homogeneous Oxidation of Alkanes by Electrophilic Late Transition Metals, Angew, Chem, Int. Ed. 1998, 2181-2192.
R. Crabtree, Aspects of Methane Chemistry, Chem. Rev., 1995, 987-1007.
A. Shilov, et al., Activation of C-H Bonds by Metal Complexes, Chem. Rev., 1997, 2879-2932.
B. Arndtsen, et al., Selective Intermolecular Carbon-Hydrogen Bond Activation by Synthetic Metal Complexes in Homogeneous Solution, Acc. Chem. Res., 1995, 154-162.
J. Labinger, Methane Activation in Homogeneous Systems, Fuel Processing Technology, 1995, Elsevier, 325-338.
T. Hall, et al., Catalytic Synthesis of Methanol and Formaldehyde by Partial Oxidation of Methane, Fuel Processing Technology, 1995, Elsevier, 151-178.
J.L.G. Fierro, Catalysis in C1 Chemistry: Future and Prospect, Catalysis Letters 22, 1993, JC Baltzer AG, Science Publishers, 67-91.
S. Mukhopadhyay, et al., Catalyzed Sulfonation of Methane to Methanesulfonic Acid, Journal of Molecular Catalysis A Chemical 211, 2004, Elvsevier, 59-65.
N. Basickes, et al., Radical-Initiated Functionalization of Methane and Ethane in Fuming Sulfuric Acid, J. Am. Chem. Soc., 1996, 13111-13112.
S. Mukhopadhyay, et al., Synthesis of Methanesulfonyl Chloride (MSC) from Methane and Sulfuryl Choloride, The Royal Society of Chemistry, 2004, 472-473.
S. Mukhopadhyay, et al., A High-Yield Approach to the Sulfonation of Methane to Methanesulfonic Acid Initiated by H2O2 and a Metal Chloride, Angew. Chem. Int. Ed, 2003, 2990.
S. Mukhopadhyay, et al., Direct Liquid-Phase Sulfonation of Methane to Methanesulfonic Acid by SO3 in the Presence of a Metal Peroxide, Angew. Chem. Int. Ed., 2003, 1019-1021.
S. Mukhopadhyay, et al., Direct Sulfonation of Methane to Methanesulfonic Acid with SO2 Using Ca Salts as Promoters, J. Am. Chem. Soc., 2003, 4406-4407.
M. Lin, et al., Oxidation and Oxidative Carbonylation of Methane and Ethane by Hexaoxo-u-peroxiodisulfate (2-) Ion in Aqueous Medium, J. Chem. Soc., 1992, 892-893.
C. Walling, Fre Radical Reactions, Energetics of Organic Free Radicals, Blackie Academic & Professional, 1-21.
G. Russell, Reactivity, Selectivity, and Polar Effects in Hydrogen tom Transfer Reactions, Free Radicals, John Wiley & Sons, 275-331.

*Primary Examiner*—Sikarl A. Witherspoon
(74) *Attorney, Agent, or Firm*—McQuaide, Blasko, Fleming & Faulkner, Inc

(57) ABSTRACT

A process for the facile two-step synthesis of methanol from methane is disclosed. In accordance with the invention, an appropriate combination of initiator and reaction medium is employed to achieve methane conversion in very high selectivity and yield under near-ambient temperature.

4 Claims, 3 Drawing Sheets

PROCESS FOR THE CONVERSION OF METHANE

RELATED APPLICATIONS

This application claims priority to Provisional Patent Application No. 60/563,717 filed Apr. 20, 2004.

GOVERNMENT SPONSORSHIP

This invention was made with support from the DOE (contract to GTL Technologies, Inc.) under Grant No. DE-FG02-03ER86160. Accordingly, the Government has certain rights in the invention.

BACKGROUND OF THE INVENTION

Methane is by far the least reactive and the most abundant member of the hydrocarbon family with known reserves similar to that of petroleum. Thus, the selective oxidative functionalization of methane to useful chemical products in high conversion and selectivity is of considerable practical importance. Most of the work in this area has involved homogeneous and heterogeneous catalysis by metal species. While there have been some notable successes, none of the systems have demonstrated the optimal combination of selectivity and yield that allows commercialization. Using potassium persulfate as an initiator, the present inventors demonstrate the sulfonation of methane in fuming sulfuric acid.

DETAILED DESCRIPTION OF THE INVENTION

Figure 1:
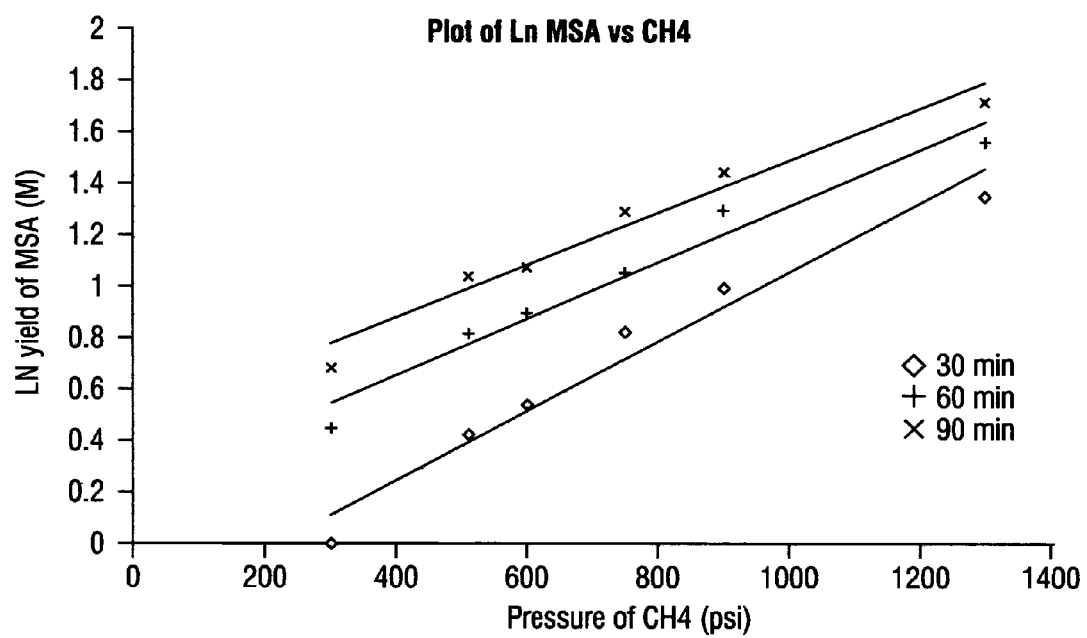
FIG. 1 is a plot of the $L_n$ of the yield for methanesulfonic acid versus the pressure of methane in pounds per square inch (used to determine the reaction order in methane) in accordance with the present invention.

The subject invention relates to a process for the manufacture of methane. In accordance with the invention, an appropriate combination of initiator and reaction medium is employed to achieve methane conversion in very high selectivity and yield under near-ambient temperature. Specifically, the invention comprises a process for conversion of methane to methanesulfonic acid ($CH_3S(O)_2OH$) by reaction with sulfur trioxide in >98% selectivity at ~50° C. In the presence of excess methane, essentially quantitative consumption of sulfur trioxide is observed with the methane conversion reaching >40%. To the inventors' knowledge, these observations are without precedent. Moreover as described in U.S. Pat. No. 2,492,983, the product, methanesulfonic acid, is known to readily form methanol by thermal extrusion of sulfur dioxide. The overall process constitutes a facile two-step synthesis of methanol from methane.

The selective conversion of methane to useful chemical products in high yield is of considerable practical importance. Basickes, et al. have described a process for converting methane to methanesulfonic acid (MSA) by reaction with sulfur trioxide using a radical initiator. The initiator used in the process was $K_2S_2O_8$. This work was followed by Mukhopadhyay, et al., who used the same initiator, as well as a variant: $H_2S_2O_8$. The present inventors have examined in detail the $H_2S_2O_8$-initiated reaction between methane and sulfur trioxide to form methanesulfonic acid (MSA). Theoretical modeling indicates that $H_2S_2O_8$ should initiate the reaction under mild conditions. A significant discovery of the experimental protocol is the combination of high conversion and selectivity that exceeds what is currently reported in the literature. Specifically:

(a) Methane conversion exceeding 35%;
(b) Sulfur trioxide conversion exceeding 90% when used as the limiting reagent;
(c) Selectivity to methanesulfonic acid exceeding 90%; and
(d) One-pass total yield of methanesulfonic acid exceeding 35%.

These reaction features, including development of the process and the high conversion and selectivity that derives from it, are described herein.

1. Synthesis of the Initiator, Peroxydisulfuric Acid ($H_2S_2O_8$)

The initiator, $H_2S_2O_8$, may be prepared by passing gaseous sulfur trioxide ($SO_3$) diluted with nitrogen gas through 70% aqueous hydrogen peroxide ($H_2O_2$) at ~20° C. until the molar ratio of $SO_3$ to $H_2O_2$ reaches 2:1. A product analysis, as described in U.S. Pat. No. 3,927,189, indicates the following: $H_2S_2O_8$, 35–55%; $H_2SO_5$, 8–20%; $H_2O_2$, 0.1–0.6%; $H_2SO_4$, 18–30%; $SO_3$, 5–10%. This solution was found to be stable at ambient temperature and under nitrogen for several weeks in the presence of a small amount of methanesulfonic acid.

2. Reaction of Methane and Sulfur Trioxide to Methanesulfonic Acid (MSA)

The reaction was carried out in a glass vessel contained in a 125 ml autoclave. A solution of $H_2S_2O_8$ was added to a mixture consisting of sulfur trioxide dissolved in methanesulfonic acid. An additional quantity of liquid $SO_3$ was then added to the autoclave. The autoclave was pressurized with 800–1400 psi of $CH_4$, and heated at 48–52° C. until the pressure stopped decreasing. The liquid reaction product was analyzed by $^1H$ NMR spectroscopy and quantified by integration versus an internal standard (DMSO in a capillary). The gas mixture in the headspace was analyzed by GC. Typical results are summarized in Table 1. Note that the amount of MSA formed is many times the amount of initiator used, establishing that the radical chain length is long with minimal termination.

TABLE 1

Yield of MSA, Conversion of $CH_4$ and $SO_3$

| Run | $H_2S_2O_8$ (mmol) | $CH_4$ (mmol) | $SO_3$ (mmol) | Time (h) | MSA Yield (mmol) | Conversion of $CH_4$ (%) | Conversion of $SO_3$ (%) |
|---|---|---|---|---|---|---|---|
| 1 | 2.9 | 240 | 101 | 14 | 97 | 40.4 | 96.0 |
| 2 | 3.2 | 266 | 109 | 12 | 108 | 40.6 | 99.1 |
| 3 | 5.5 | 319 | 149 | 10 | 138 | 43.3 | 92.6 |
| 4 | 5.8 | 372 | 135 | 6 | 125 | 33.6 | 92.6 |

As can be seen from the table, conversion of the limiting reagent, sulfur trioxide, is nearly quantitative while that of methane exceeds 40%. The selectivity for MSA in the liquid is over 99%, with less than 1% of the following combined:

$CH_3OS(O)_2OH$, $(CH_3O)_2SO_2$, $CH_3S(O)_2OCH_3$, and $CH_2(S(O)_2OH)_2$. The analysis of the gaseous products indicated the formation of trace amounts of CO and $CO_2$ with a combined yield ~0.5%.

3. Mechanism and Kinetic Study

The following are the initiation and termination steps of the reaction (Eqs. 1–4). The facile H-atom abstraction from methane by $KOS(O)_2O\bullet$ has been previously demonstrated. (N. Basickes, T. E. Hogan, A. Sen, *J. Am. Chem. Soc.*, 1996, 118, 13111; M. Lin and A. Sen, *J. Am. Chem. Soc., Chem. Commun.*, 1992, 892). The preference for H-atom abstraction from methane rather than the methyl group of MSA ($CH_3S(O)_2OH$) by $CH_3S(O)_2O\bullet$ can be ascribed at least in part to the electrophilic nature of the radical (polar effect).

Initiation:

$$H_2S_2O_8 \rightarrow 2HOS(O)_2\bullet \quad (1)$$

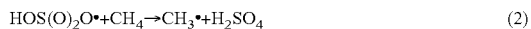
$$HOS(O)_2\bullet + CH_4 \rightarrow CH_3\bullet + H_2SO_4 \quad (2)$$

Propagation:

$$CH_3\bullet + SO_3 \rightarrow CH_3S(O)_2O\bullet \quad (3)$$

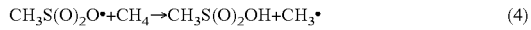
$$CH_3S(O)_2O\bullet + CH_4 \rightarrow CH_3S(O)_2OH + CH_3\bullet \quad (4)$$

During propagation, one radical is destroyed but another is created. Therefore, total concentration of radicals, [R•], in the propagation sequence remains constant. Thus, under steady state conditions, the total concentration of radicals is:

$$d[R\bullet]/dt = 0 = \text{rate of initiation } (r_i) - \text{rate of termination } (r_t)$$

$r_i = 2k_i[H_2S_2O_8]$; $r_t = 2k_t[R\bullet]^2$ (assuming bimolecular termination)

Now, rate of propagation $(r_p) = k_p[R\bullet][CH_4]$ (assuming this is slower of the two propagation steps; $CH_3\bullet + SO_3$ should be fast)

But, $[R\bullet] = \{2k_i[H_2S_2O_8]/2k_t\}^{1/2} = (k_i/k_t)^{1/2}[H_2S_2O_8]^{1/2}$ (5)

Therefore, rate of propagation $(r_p) = k_p(k_i/k_t)^{1/2}[H_2S_2O_8]^{1/2}[CH_4]$ (6)

In order to determine the actual reaction orders in methane and $H_2S_2O_8$, a series of experiments were run. In the first, approximately 2.0–3.0 g of $H_2S_2O_8$ solution was added to 14.0–17.0 g of a mixture of $SO_3$ and MSA in a glass liner in an autoclave. The reaction system was pressurized with 300–1300 psi of $CH_4$ and heated at 54–56° C. The progress of the reaction was followed by monitoring the drop in methane pressure, the assumption being that the concentration of methane in solution is proportional to the methane pressure. During the initial stages of the reaction (up to 90 min), the rate was found to be approximately first order in methane (FIG. 1) within the pressure range examined.

Figure 2:
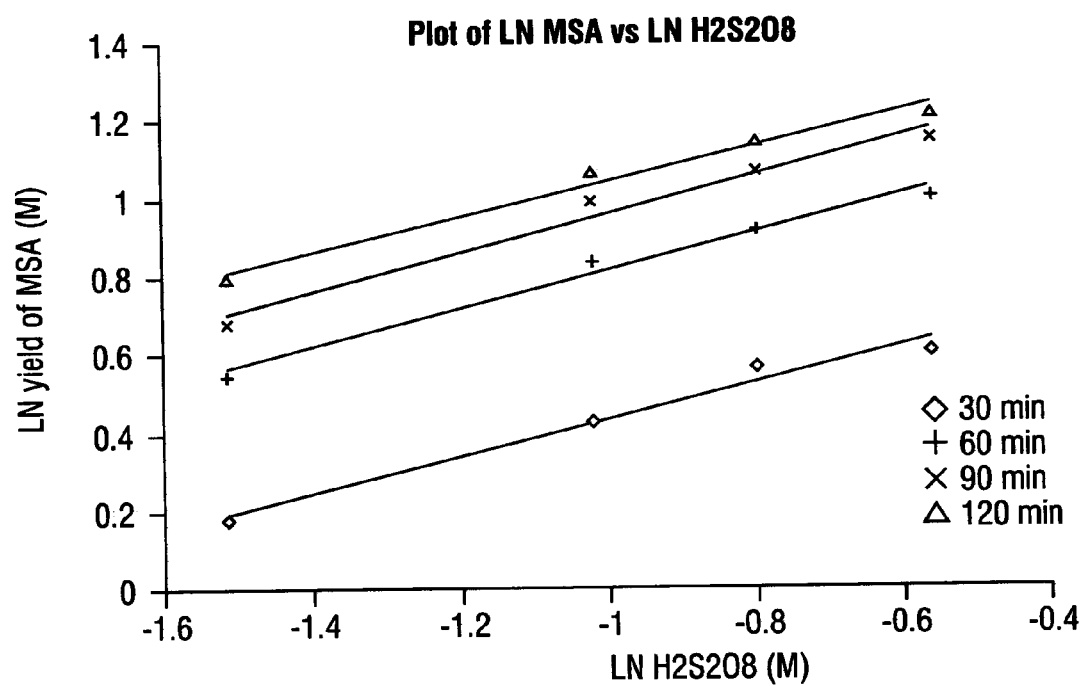
FIG. 2 is a plot of the $L_n$ of the yield for peroxydisulfuric acid versus the pressure of methane in pounds per square inch (used to determine the reaction order in $H_2S_2O_8$) in accordance with the present invention.

In order to examine the reaction order in $H_2S_2O_8$, a similar set of experiments were carried out at 54–56° C. where the initial methane pressure was set at 500 psi. In this instance, during the initial stages of the reaction (up to 120 min), the rate was found to be approximately half order in $H_2S_2O_8$ (FIG. 2). Thus, within error limits, the experimental results support the mechanistic model described above with the rate of propagation given by:

$$R_p = k[H_2S_2O_8]^{1/2}[CH_4] \quad (7)$$

4. Determination of Activation Energy

Figure 3:
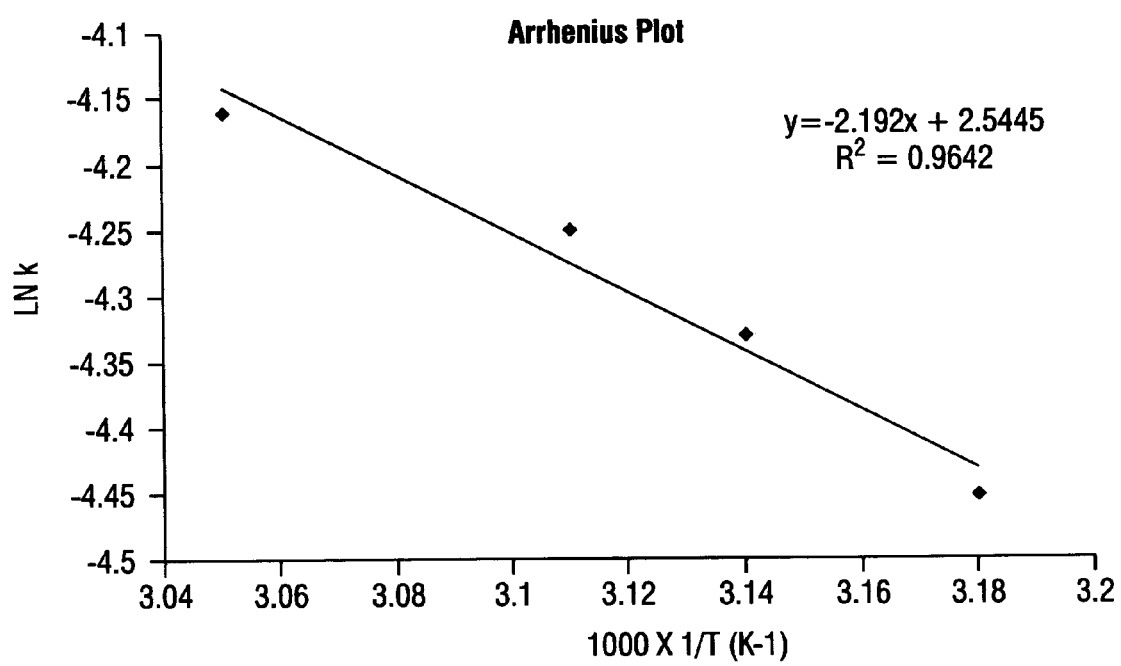
FIG. 3 is a plot of the $L_n$ of the rate constant for methanesulfonic acid production versus $1000 \times 1/T$ in Kelvin (used to determine the activation energy parameters for the reaction) in accordance with the present invention.

In order to determine the overall activation energy for the process, the reaction was run at several temperatures between 41 and 55° C. The initial methane pressure was set at 1300 psi. Evaluation of the rate constant of Eq. (7) requires knowledge of the concentration of methane in the reaction medium. The solubility of methane at 1 atm (14.7 psi) in $MSA/SO_3$ mixture was measured, and found to be 0.0022M at 20° C. and 0.0021M at 24° C. The concentrations of methane at higher pressures were calculated assuming Henry's law, i.e. the solution concentration was proportional to the pressure. Using the above assumption, the rate constant for the reaction was evaluated at different temperatures and an Arrhenius plot was constructed (FIG. 3). The plot is clearly linear and yields an activation energy, $E_a = 18.2$ kJ $mol^{-1}$ and $A = 12.7$ $M^{-1/2} sec^{-1}$. Despite the approximations inherent in these calculations, the activation energy associated with H-atom abstraction from methane (Eq. 4 above, the most likely rate-limiting step) is remarkably low and further suggests the utility of radical-initiated functionalization of methane.

In sum, the present invention shows that $H_2S_2O_8$ is an efficient initiator for the reaction of methane with sulfur trioxide to form methanesulfonic acid at ~50° C. The radical chain length is long with minimal termination. Selectivity for MSA is >98%. When used as the limiting reagent, the conversion of sulfur trioxide is nearly quantitative with methane conversion >40%. The reaction is first-order in methane and half-order in $H_2S_2O_8$ and the activation energy is quite low: $E_a = 18.2$ kJ $mol^{-1}$ (4.35 kJ $mol^{-1}$).

There are several features of the instant system that distinguish it from others reported previously. Primarily, the reaction medium, MSA, is also the reaction product, thus obviating the need for a product separation step. The observed high selectivity and yield derives from two factors. First, sulfur trioxide is an efficient trapping agent for methyl radicals. Second, the methyl group in the product, MSA, is deactivated due to the vicinal electron-withdrawing —$S(O)_2OH$ fragment. As a result overoxidation of the product is avoided.

While the invention has been particularly shown and described with reference to preferred embodiments thereof, it will be understood by those skilled in the art that various alterations in form and detail may be made therein without departing from the spirit and scope of the invention.

What is claimed is:

1. A process for converting methane to methanesulfonic acid, whereby methane conversion exceeds 35% of total methane, comprising:
    a) dissolving $H_2S_2O_8$ in a mixture of methanesulfonic acid and sulfur trioxide; and
    b) contacting methane at 300 to 1400 psi with a solution resulting from said mixture at about 40–60° C.

2. A process for converting methane to methanesulfonic acid, whereby sulfur trioxide conversion exceeds 90% of total sulfur trioxide when used as the limiting reagent, comprising:
    a) dissolving $H_2S_2O_8$ in a mixture of methanesulfonic acid and sulfur trioxide; and
    b) contacting methane at 300 to 1400 psi with a solution resulting from said mixture at about 40–60° C.

3. A process for converting methane to methanesulfonic acid, whereby selectivity to methanesulfonic acid exceeds 90% of total product, comprising:
    a) dissolving $H_2S_2O_8$ in a mixture of methanesulfonic acid and sulfur trioxide; and
    b) contacting methane at 300 to 1400 psi with a solution resulting from said mixture at about 40–60° C.

4. A process for converting methane to methanesulfonic acid, whereby the one-pass yield of methanesulfonic acid exceeds 35% of total methane, comprising:
 a) dissolving $H_2S_2O_8$ in a mixture of methanesulfonic acid and sulfur trioxide; and
 b) contacting methane at 300 to 1400 psi with a solution resulting from said mixture at about 40–60° C.

* * * * *

(12) EX PARTE REEXAMINATION CERTIFICATE (6922nd)
United States Patent
Sen et al.

(10) Number: US 7,119,226 C1
(45) Certificate Issued: Jul. 7, 2009

(54) PROCESS FOR THE CONVERSION OF METHANE

(75) Inventors: Ayusman Sen, State College, PA (US); Minren Lin, State College, PA (US)

(73) Assignee: The United States of America as represented by the United States Department of Energy, Washington, DC (US)

Reexamination Request:
No. 90/008,925, Jan. 22, 2008

Reexamination Certificate for:
Patent No.: 7,119,226
Issued: Oct. 10, 2006
Appl. No.: 11/105,245
Filed: Apr. 13, 2005

Related U.S. Application Data
(60) Provisional application No. 60/563,717, filed on Apr. 20, 2004.

(51) Int. Cl.
*C07C 309/00* (2006.01)

(52) U.S. Cl. ..................................................... 562/123
(58) Field of Classification Search ....................... None
See application file for complete search history.

(56) References Cited

FOREIGN PATENT DOCUMENTS

WO    WO 2004/041399    5/2004

OTHER PUBLICATIONS

Basickles, et al., Radical–Initiated Functionalization of Methane and Ethane in Fuming Sulfuric Acid, J. Am. Chem. Soc. 118 (51), 13111–13112, 1996.

*Primary Examiner*—Brenda Brumback

(57) ABSTRACT

A process for the facile two-step synthesis of methanol from methane is disclosed. In accordance with the invention, an appropriate combination of initiator and reaction medium is employed to achieve methane conversion in very high selectivity and yield under near-ambient temperature.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–4 is confirmed.

* * * * *